(12) United States Patent
Schuhmacher et al.

(10) Patent No.: US 8,486,443 B2
(45) Date of Patent: Jul. 16, 2013

(54) UV STABLE TRANSDERMAL THERAPEUTIC PLASTER WITH A UV ABSORBING ADHESIVE LAYER SEPARATED FROM THE DRUG MATRIX

(75) Inventors: Jochen Schuhmacher, Bucha (DE); Manfred Suesse, Langenorla (DE); Michael Dittgen, Apolda (DE); Stephan Mletzko, Berlin (DE); Jan-Peter Ingwersen, Berlin (DE); Thomas Langguth, Jena (DE); Dirk Schenk, Dietramszell (DE); Hubert Kaffl, Fischbachau (DE)

(73) Assignee: Bayer IP GmbH, Berlin (DE)

( * ) Notice: Subject to any disclaimer, the term of this patent is extended or adjusted under 35 U.S.C. 154(b) by 1830 days.

(21) Appl. No.: 10/545,826

(22) PCT Filed: Feb. 4, 2004

(86) PCT No.: PCT/EP2004/001052
§ 371 (c)(1),
(2), (4) Date: May 26, 2006

(87) PCT Pub. No.: WO2004/073696
PCT Pub. Date: Sep. 2, 2004

(65) Prior Publication Data
US 2006/0251707 A1 Nov. 9, 2006

(30) Foreign Application Priority Data

Feb. 21, 2003 (EP) .................................... 03003888
Feb. 25, 2003 (EP) .................................... 03004061

(51) Int. Cl.
*A61K 9/70* (2006.01)
(52) U.S. Cl.
USPC .......................................... 424/449; 424/448
(58) Field of Classification Search
None
See application file for complete search history.

(56) References Cited

U.S. PATENT DOCUMENTS

| 5,023,084 | A | 6/1991 | Chien et al. |
|---|---|---|---|
| 5,106,891 | A | 4/1992 | Valet |
| 5,128,124 | A | 7/1992 | Fankhauser et al. |
| 5,128,284 | A | 7/1992 | Olson et al. |
| 5,248,676 | A | 9/1993 | Nakagawa et al. |
| 5,352,457 | A | 10/1994 | Jenkins |
| 5,376,377 | A | 12/1994 | Gale et al. |
| 5,512,292 | A | 4/1996 | Gale et al. |
| 5,538,736 | A | 7/1996 | Hoffmann et al. |
| 5,560,922 | A | 10/1996 | Chien et al. |
| 5,762,956 | A | 6/1998 | Chien et al. |
| 5,788,984 | A | 8/1998 | Guenther et al. |
| 5,858,394 | A * | 1/1999 | Lipp et al. ...................... 424/449 |
| 5,866,157 | A | 2/1999 | Higo et al. |
| 5,904,931 | A | 5/1999 | Lipp et al. |
| 5,906,830 | A | 5/1999 | Farinas et al. |
| 5,948,433 | A | 9/1999 | Burton et al. |
| 6,071,531 | A | 6/2000 | Jona et al. |
| 6,143,319 | A | 11/2000 | Meconi et al. |
| 6,238,284 | B1 | 5/2001 | Dittgen et al. |
| 6,521,250 | B2 | 2/2003 | Meconi et al. |
| 6,902,741 | B1 | 6/2005 | Grawe et al. |
| 6,924,410 | B2 | 8/2005 | Tsuruda et al. |
| 7,470,452 | B1 | 12/2008 | Flosbach et al. |
| 7,687,554 | B2 | 3/2010 | Schellenberg et al. |
| 8,173,592 | B1 | 5/2012 | Engel et al. |
| 2002/0004065 | A1 | 1/2002 | Kanios et al. |
| 2003/0149385 | A1 * | 8/2003 | Tsuruda et al. .................. 602/20 |
| 2003/0152616 | A1 | 8/2003 | Hartwig et al. |
| 2004/0022836 | A1 * | 2/2004 | Degen et al. .................. 424/449 |
| 2005/0055975 | A1 | 3/2005 | Tackett et al. |
| 2005/0142175 | A1 | 6/2005 | Langguth et al. |
| 2005/0175678 | A1 | 8/2005 | Breitenbach et al. |
| 2006/0246122 | A1 | 11/2006 | Langguth et al. |
| 2006/0251707 | A1 | 11/2006 | Schumacher et al. |
| 2008/0063698 | A1 | 3/2008 | Hartwig et al. |

FOREIGN PATENT DOCUMENTS

| CA | 2 372 710 | 8/2000 |
|---|---|---|
| CA | 2 366 859 | 9/2001 |
| CA | 2 605 112 | 11/2006 |
| DE | 43 36 299 | 5/1995 |
| DE | 43 36 299 A1 | 5/1995 |
| DE | 44 03 487 | 8/1995 |
| DE | 44 03 487 A1 | 8/1995 |

(Continued)

OTHER PUBLICATIONS

M. Brisaert et al: "Investigation on the Photostability of a . . . " Proc 2-nd World Meeting APGI/APV, Paris, May 25-28, 1998, pp. 1231-1232 (in English).
Translation of Abstract of JP-10265371, Publication Date: Oct. 6, 1998.
Translation of Abstract of JP-530118, Publication Date: Mar. 10, 2004.
Translation of Abstract of JP-59039827, Publication Date: Mar. 5, 1984.
Translation of Abstract of JP-60 069014, Publication Date: Apr. 19, 1985.
Translation of Abstract of JP-60166611, Publication Date: Aug. 29, 1985.
Shinyosha:KK, "Image display apparatus and pixel constituent," Patent Abstracts of Japan, Publication Date: Jan. 5, 2006; English Abstract of JP-4 504109.

(Continued)

*Primary Examiner* — Kevin S Orwig
(74) *Attorney, Agent, or Firm* — Millen, White, Zelano, Branigan, P.C.

(57) ABSTRACT

The invention relates to a UV stable transdermal therapeutic system (TTS) consisting of a back layer, at least one matrix containing an active substance and, optionally, a withdrawal film and an UV-radiation absorber. An adhesive layer containing said UV-radiation absorber is arranged between the back layer and the matrix containing an active substance which is distant as much as possible from a surface, a separation layer is arranged between the adhesive layer containing said UV-radiation absorber and the matrix containing an active substance, which is as remote as possible from the surface which is impermeable to the active substance and UV radiation absorber. The inventive transdermal therapeutic system exhibits a high stability and is devoid of inconveniences of existing TTS containing a light-sensitive substance.

22 Claims, No Drawings

FOREIGN PATENT DOCUMENTS

| | | |
|---|---|---|
| DE | 199 06 152 | 8/2000 |
| DE | 199 12 623 A | 9/2000 |
| DE | 199 12 623 A1 | 9/2000 |
| DE | 100 53 375 | 1/2002 |
| DE | 100 53 375 C1 | 1/2002 |
| EP | 0 285 563 | 10/1988 |
| EP | 0 483 370 | 3/1995 |
| EP | 0 787 488 | 8/1997 |
| EP | 976 405 | 2/2000 |
| EP | 1 121 941 | 8/2001 |
| EP | 1 197 212 | 4/2002 |
| EP | 1 269 999 | 1/2003 |
| EP | 1 452 173 | 9/2004 |
| EP | 1 541 137 | 6/2005 |
| JP | 59039827 | 3/1984 |
| JP | 60 069014 | 4/1985 |
| JP | 60166611 | 8/1985 |
| JP | 10-26537 A1 | 1/1989 |
| JP | 6 93217 | 4/1994 |
| JP | 09 315957 | 12/1997 |
| JP | 10-265371 | 10/1998 |
| JP | 10265371 | 10/1998 |
| JP | 2002 541122 | 12/2000 |
| JP | 530118 | 3/2004 |
| JP | 4 504109 | 1/2006 |
| WO | WO-90/04397 | 5/1990 |
| WO | WO-90 06736 | 6/1990 |
| WO | WO-92/07590 | 5/1992 |
| WO | WO-96 40355 | 12/1996 |
| WO | WO-97 38354 | 10/1997 |
| WO | WO-97/39743 | 10/1997 |
| WO | WO-99 66908 | 12/1999 |
| WO | WO-00/45797 | 8/2000 |
| WO | WO-00/56289 | 9/2000 |
| WO | WO-00 59542 | 10/2000 |
| WO | WO-01/37770 | 5/2001 |
| WO | WO 01/68061 * | 9/2001 |
| WO | WO-01 68061 | 9/2001 |
| WO | 02/34200 | 5/2002 |
| WO | WO-02/45701 | 6/2002 |
| WO | WO-03 077925 | 9/2003 |
| WO | WO-2004 058247 | 7/2004 |
| WO | WO-2004 073696 | 9/2004 |
| WO | WO-2005 023878 | 3/2005 |
| WO | WO-2005 058287 | 6/2005 |
| WO | WO-2006 117139 | 11/2006 |
| WO | WO-2010 042152 | 4/2010 |

OTHER PUBLICATIONS

Bjarnason et al., "Low doses of estradiol in combination with gestodene to prevent postmenopausal bone loss," American Journal of Obstetrics and gynecology, Sep. 2000, vol. 183, No. 3, pp. 550-560.

Chatelain, Eric et al., "Photostabilization of Butyl Methozydibenzoylmethane . . . " Photochemistry and Photobiology, 2001, vol. 74, No. 3, pp. 401-406 (English).

Ciba Specialty Chemicals Tinosorb S brochure (2002).

European Search Report dated May 12, 2004.

Partial European Search Report dated Sep. 27, 2005.

Sitruk-Ware, R., "Transdermal Application of Steroids Hormones for Contraception," J. Steroid Biochem. Molec. Biol., 1995, vol. 53, No. 1-6, pp. 247-251.

Thomson Innovation, English Translation of Claims and Description, Retrieved from Thomson Innovation Record View on Jun. 14, 2010; English Abstract of WO1990004397.

Thomson Innovation, English Translation of Claims and Description, Retrieved from Thomson Innovation Record View on Jun. 14, 2010; English Abstract of WO2000056289.

Thomson Innovation, English Translation of Claims and Description, Retrieved from Thomson Innovation Record View on Jun. 14, 2010; English Abstract of EP1452173.

Thomson Innocation, English Translation of Claims and Description, Retrieved from Thomas Innovation Record View on Jul. 26, 2010; English Abstract of DE4336299.

Thomson Innocation, English Translation of Claims and Description, Retrieved from Thomas Innovation Record View on Jul. 26, 2010; English Abstract of DE 4403487.

Thomson Innocation, English Translation of Claims and Description, Retrieved from Thomas Innovation Record View on Jul. 26, 2010; English Abstract of DE19912623.

Sanken Kako KK, "Production of dibenxyls," Patent Abstracts of Japan, Publication Date: Jan. 27, 1989, English Abstract of JP-10-256371.

Hisamitsu Pharmaceut Co Inc., "Device for percutaneous therapy," Patent Abstracts of Japan, Publication Date: Dec. 9, 1997; English Abstract of JP-09 315957.

Sekisui Chem Co Ltd., "Transcutaneous Absorption Plaster," Patent Abstract of Japan, Publication Date: Oct. 6, 1998; Full English Translation of JP-10 265371.

* cited by examiner

UV STABLE TRANSDERMAL THERAPEUTIC PLASTER WITH A UV ABSORBING ADHESIVE LAYER SEPARATED FROM THE DRUG MATRIX

CROSS-REFERENCE TO RELATED APPLICATIONS

This is the US National Stage of PCT/EP 04/01052, filed on 4 Feb. 2004, and claims the priority under 35 U.S.C. 119(a)-(d) to European Patent Application No. 03 004 061.2, filed 25 Feb. 2003 and to European Patent Application No. 03 003 888.9, filed 21 Feb. 2003.

BACKGROUND OF THE INVENTION

1. Field of the Invention

The invention relates to a novel UV-stable transdermal therapeutic system (TTS) which consists of a backing layer, of at least one active ingredient-containing matrix and optionally of a detachable sheet, and comprises a UV absorber, with at least one UV absorber-containing adhesive layer being provided between the backing layer and the active ingredient-containing matrix which is furthest away from the surface of the skin, and at least one separating layer which is impermeable to active ingredient and impermeable to the UV absorber being present between the adhesive layer containing the UV absorber and the active ingredient-containing matrix which is furthest away from the surface of the skin.

2. Description of the Related Art

Attempts are known to employ photosensitive active ingredients which absorb UV-A and UV-B rays and normally in suncreams as described by Briscart & Plaizier-Vercammen (Proc. 2nd World Meeting on Pharmaceutics, Biopharmaceutics and Pharmaceutical Technology, APGI/APV, 1998, 1231-1232).

It is additionally known to protect transdermal therapeutic systems provided with photosensitive active ingredients by means of visually noticeable aluminized or lacquered cover sheets as backing layer of the TTS. DE-A1-19912623 describes a method for protecting therapeutic preparations, systems or ingredients thereof, the intention being to achieve protection, specific in each case, against breakdown by harmful factors such as atmospheric oxygen, water and/or light. Photoprotective substances which absorb or reflect electromagnetic waves are used, employing absorbing or reflecting agents whose absorption or reflection spectrum covers the wavelength range responsible for the instability of the photosensitive material or its ingredients. Coloured plastic sheets are used inter alia as cover sheet in this case, shown by the example of the 1,4-dihydropyridine derivative lacidipine.

The colouring of highly flexible plastic sheets proves to be difficult and does not provide reliable protection from light owing to fissures which frequently occur in the coloured layer of the plastic sheet.

Furthermore, DE-C1-10053375 discloses transdermal therapeutic systems (TTS) which consist of an active ingredient-containing polymer matrix and a backing layer, with polymer matrix and backing layer being firmly connected and forming a laminate, and both the polymer matrix and the backing layer containing a colourless substance which absorbs in the UV region and which has no intrinsic pharmacological effect. This solution is disadvantageous in that interaction of the colourless substance which absorbs in the UV region with the active ingredient in the polymer matrix in some cases results in an unwanted influence on the stability of the TTS, in that the firm connection between polymer matrix and backing layer which is permeable to active ingredient may result in extensive unacceptable diffusion of active ingredient from the polymer matrix into the backing layer, principally in the case of backing layers composed of polypropylene, polyethylene or polyurethane, and may finally emerge or crystallize out on the upper side of the backing layer/cover sheet, in that skin irritation may be caused through direct contact of the skin with the substances which absorb in the UV region and which are present in the backing layer/cover sheet.

It is therefore an object of the invention to provide a pharmaceutical preparation which is provided with a photosensitive active ingredient and is to be administered transdermally, and which achieves high stability without the aforementioned disadvantages.

BRIEF SUMMARY OF THE INVENTION

The object is achieved according to the invention by a transdermal therapeutic system (TTS) consisting of a backing layer, of at least one active ingredient-containing matrix and optionally of a detachable sheet, and comprising a UV absorber, with at least one UV absorber-containing adhesive layer being provided between the backing layer and the active ingredient-containing matrix which is furthest away from the surface of the skin, and at least one separating layer which is impermeable to active ingredient and impermeable to the UV absorber being present between the adhesive layer containing the UV absorber and the active ingredient-containing matrix which is furthest away from the surface of the skin.

DETAILED DESCRIPTION OF THE INVENTION

The sequence of layers of the transdermal therapeutic system starting from the side facing away from the skin can according to the invention be backing layer, UV absorber-containing adhesive layer, separating layer and finally a mono- or bilayer active ingredient-containing matrix whose pressure-sensitive adhesive surface is covered by a detachable protective sheet. The separating layer in the transdermal therapeutic system may moreover have according to the invention a layer thickness of from 4 to 23 µm, preferably from 4 to 10 µm, and consist of a barrier polymer. Suitable barrier polymers are polyethylene terephthalate, polyacrylonitrile, polyvinyl chloride, polyvinylidene chloride or its copolymers or colaminates. The matrix in the transdermal therapeutic system of the invention may be designed to be self-adhesive and have no membrane controlling the release of active ingredient, and consist essentially of polymers selected from the group of polyisobutylene, polybutene, polyacrylate, polydimethylsiloxane, styrene/isoprene block copolymer or polyisoprene. The weight per unit area of the matrix can be according to the invention from 30 to 150 g/m$^2$, preferably 50 to 120 g/m$^2$, particularly preferably about 100 g/m$^2$.

The backing layer in the transdermal therapeutic system of the invention may be a transparent sheet from the group of polypropylene, polyethylene, polyurethane, polyester, ethylene/vinyl acetate copolymer or polyethylene terephthalate or mixtures thereof and may be permeable to active ingredient.

The UV absorber in the adhesive layer in the transdermal therapeutic system of the invention may moreover be present in dissolved form in a concentration of 0.5 to 10% (m/m), preferably 1.0 to 5.0% (m/m), particularly preferably 2.0 to 4.0% (m/m), and the adhesive layer may be designed to be self-adhesive and consist essentially of polymers selected from the group of polyisobutylene, polybutene, polyacrylate, polydimethylsiloxane, styrene/isoprene block copolymer or polyisoprene. The adhesive layer may moreover have a weight per unit area of from 5 to 50 g/m², preferably 20 to 30 g/m².

The adhesive layer in the transdermal therapeutic system of the invention may also have exclusively the UV absorber(s), it being possible for the latter to be colourless or yellowish.

The adhesive layer in the transdermal therapeutic system of the invention may moreover have a UV absorber content composed of a mixture of two or more substances which absorb in the UV region, it being possible to select the UV absorber(s) from the group of p-amino-benzoic acid, aminobenzoic acid derivative, preferably 2-ethylhexyl 4-dimethylaminobenzoate and/or polyethoxy-ethyl 4-bis(polyethoxyl)aminobenzoate, cinnamic acid, cinnamic acid derivatives, preferably isoamyl 4-methoxycinnamate and/or 2-ethylhexyl 4-methoxycinnamate, 3-benzylidenebornan-2-one, benzylidenebornan-2-one derivatives, preferably 3-(4')-methylbenzylindenebornan-2-one, 3-(4-sulphone)-benzylidenebornan-2-one and/or 3-(4'-trimethyl-ammonium) benzylidenebornan-2-one methylsulphate, salicylic acid derivative, preferably 4-isopropylbenzyl salicylate, 2-ethylhexyl salicylate, and/or 3,3,5-trimethylcyclohexyl salicylate, benzotriazoles, preferably 2-(5-chloro-2H-benzotriazole-2-yl)-6-(1,1-dimethylethyl)-4-methylphenol, 2,4,6'-trianiline-p-(carbo-2'-ethylhexyl-1'-oxy)-1,3,5-triazine, 3-imidazol-4-ylacrylic acid, 3-imidazol-4-yl-3-imidazol-4-ylacrylic ester, 2-phenylenebenzimidazole-5-sulphonic acid and/or its K, Na and triethanolamine (=TEA) salts, 2-cyano-3,3-diphenylacrylic acid, terephthaloylidenedicamphorsulphonic acid, butyl-methoxydibenzoylmethane, benzophenone and/or benzophenone derivatives, preferably benzophenone-3 and/or benzophenone-4. The UV absorber(s) may moreover be colourless or yellowish.

A further possibility is for the transdermal therapeutic system of the invention to be transparent or slightly opaque.

The active pharmaceutical ingredient acting in the transdermal therapeutic system of the invention may be at least one hormone and be progestogen(s), preferably gestodene or levonorgestrel.

The transdermal therapeutic system of the invention has the following advantages over conventional systems with photosensitive active ingredient content:

It is possible by varying the thickness of the layer containing the UV absorber or the concentration of the UV absorber therein to adjust accurately the desired UV protection. This is a considerable advantage over the use of conventional TTS with incorporated UV protection.

Contact between the UV absorber and the active ingredient or active ingredients in the active ingredient-containing matrix is precluded, so that neither the UV absorber nor its breakdown products which may arise under the influence of light can react with the active ingredient(s).

If a cover sheet which is permeable to active ingredient is used, diffusion of active ingredient on storage of the system may reach unacceptably high levels, so that active ingredient may emerge or crystallize out on the surface of the cover sheet. This effect can be observed for example with cover sheets composed of polypropylene, polyethylene or polyurethane. The separating layer provided according to the invention between the layer with UV absorber and the active ingredient-containing layer now represents a barrier against loss of active ingredient by diffusion through the cover sheet.

In addition, contact of the skin with UV absorbers, and thus possible skin irritation, can be avoided.

The invention and its advantageous properties are explained in detail by the following examples.

Example 1

Two formulations of a photosensitive active ingredient from the group of progestogens were produced. Formulation I contains an adhesive layer and a separating layer, with the adhesive layer containing 3% by weight of a UV-absorbing substance.

Formulation II contains no adhesive layer and separating layer and serves as comparative formulation. Both formulations contain an active ingredient-containing matrix with a photosensitive progestogen and were provided with a polyethylene backing layer, resulting in a TTS in each case.

Formulation I has the following composition:
1. Active Ingredient-Containing Matrix:
   1.9% progestogen
   98.1% polyisobutylene-based adhesive
2. Adhesive Layer:
   3% Tinuvin® 326
   97% polyisobutylene-based adhesive Tinuvin®326 (from CIBA, Lampertheim) is a UV absorber of the hydroxyphenylbenzotriazole class.

To investigate the light protection effect, both formulations were irradiated with light having a UV spectrum of 300-800 nm over a period of up to 14 h. The radiation source used was a xenon lamp. A filter system (type: Suprax® filter) was placed between the radiation source and the samples to be irradiated in order to simulate the irradiation under realistic conditions of TTS use. The active ingredient content in the TTS was then determined. It emerged that the TTS of formulation A containing an adhesive layer with UV-absorbing substance and a separating layer still contained about 99% of the originally employed amount of the photosensitive active ingredient after irradiation for 14 h, whereas the TTS of formulation B contained only about 24% of the originally employed amount of the photosensitive active ingredient after irradiation for only 7 h (FIG. 1). This shows that the system of the invention displays improved protection from the sun under realistic conditions of use, because the UV-protective effect of the system of the invention (formulation A) was considerably greater than that of the comparative system (formulation B).

Example 2

Formulation with a photosensitive active ingredient from the group of progestogens with, in each case, an adhesive layer and separating layer, in which the separating layers consists of polyethylene terephthalate (Hostaphan® from Mitsubishi Polyester, Wiesbaden).

The formulation has the following composition:
1. Active Ingredient-Containing Matrix:
   1.9% progestogen
   98.1% polyisobutylene-based adhesive
2. Adhesive Layer 1 and 2:
   3% Uvinul®MC80
   97% polyacrylate-based adhesive Uvinul®MC 80 (from BASF, Ludwigshafen) is a methoxy-cinnamic acid derivative.

Example 3

Formulation with a photosensitive active ingredient from the group of progestogens with, in each case, two adhesive layers and separating layers, in which the separating layers consist of polyethylene terephthalate (Hostaphan® from Mitsubishi Polyester, Wiesbaden).

Formulation I has the following composition:

3. Active Ingredient-Containing Matrix:
   1.9% progestogen
   98.1% polyisobutylene-based adhesive
4. Adhesive Layer 1 and 2:
   3% Uvinul®M40
   97% polyacrylate-based adhesive Uvinul®M40 (from BASF, Ludwigshafen) is a benzophenone derivative.

Example 4 to 12

Formulation with a photosensitive active ingredient from the group of progestogens with, in each case, at least one adhesive layer and separating layer, in which the active ingredient-containing matrix is configured in analogy to Examples 1 to 3, and the adhesive layer comprises a polyisobutylene-based adhesive and has the following compositions.

| Composition of the adhesive layer | Example 4 | Example 5 | Example 6 | Example 7 | Example 8 | Example 9 | Example 10 | Example 11 | Example 12 |
|---|---|---|---|---|---|---|---|---|---|
| Tinuvin® 326 [%] | 2 | 2 | 2 | 3 | 3 | 3 | 4 | 4 | 4 |
| Polyisobutylene-based adhesive [%] | 98 | 98 | 98 | 97 | 97 | 97 | 96 | 96 | 96 |
| Weight per unit area [g/m²] | 20 | 30 | 50 | 20 | 30 | 50 | 20 | 30 | 50 |

Example 13 to 21

Formulation with a photosensitive active ingredient from the group of progestogens with, in each case, at least one adhesive layer and separating layer, in which the active ingredient-containing matrix is configured in analogy to Examples 1 to 3, and the adhesive layer comprises a polyacrylate-based adhesive and has the following compositions.

| Composition of the adhesive layer | Example 13 | Example 14 | Example 15 | Example 16 | Example 17 | Example 18 | Example 19 | Example 20 | Example 21 |
|---|---|---|---|---|---|---|---|---|---|
| Tinuvin® 326 [%] | 2 | 2 | 2 | 3 | 3 | 3 | 4 | 4 | 4 |
| Polyacrylate-based adhesive [%] | 98 | 98 | 98 | 97 | 97 | 97 | 96 | 96 | 96 |
| weight per unit area [g/m²] | 20 | 30 | 50 | 20 | 30 | 50 | 20 | 30 | 50 |

Example 22 to 30

Formulation with a photosensitive active ingredient from the group of progestogens with, in each case, at least one adhesive layer and separating layer, in which the active ingredient-containing matrix is configured in analogy to Examples 1 to 3, and the adhesive layer has the following compositions.

| Composition of the adhesive layer | Example 22 | Example 23 | Example 24 | Example 25 | Example 26 | Example 27 | Example 28 | Example 29 | Example 30 |
|---|---|---|---|---|---|---|---|---|---|
| Uvinul® MC80 | 2 | 5 | 8 | — | — | — | — | — | — |
| Uvinul® M40 | — | — | — | 2 | 5 | 8 | 2 | 5 | 8 |

-continued

| Composition of the adhesive layer | Example 22 | Example 23 | Example 24 | Example 25 | Example 26 | Example 27 | Example 28 | Example 29 | Example 30 |
|---|---|---|---|---|---|---|---|---|---|
| Polyisobutylene-based adhesive [%] | 98 | 95 | 92 | 98 | 95 | 92 | — | — | — |
| Polyacrylate-based adhesive [%] | — | — | — | — | — | — | 98 | 95 | 92 |
| Weight per unit area [g/m$^2$] | 20 | 30 | 50 | 20 | 30 | 50 | 20 | 30 | 50 |

The invention claimed is:

1. A transdermal therapeutic system consisting of: a backing layer, one or more UV absorber-containing layers, a separating layer, one or more active ingredient-containing matrices, and optionally a detachable sheet wherein
   the one or more UV absorber-containing layers are provided between the backing layer and the separating layer, and the separating layer is provided between the one or more UV absorber-containing layers and the one or more active ingredient-containing matrices,
   an active ingredient-containing matrix and a UV absorber-containing layer are self-adhesive and comprise a polymer selected from the group consisting of polyisobutylene, polybutene, polyacrylate, styrene/isoprene block polymer, polyisoprene and combinations thereof,
   the separating layer is impermeable to the active ingredient and impermeable to the UV absorber, and
   the separating layer has a layer thickness of from 4 to 10 μm.

2. The transdermal therapeutic system according to claim 1, consisting of the following sequence of layers: a backing layer, a UV absorber-containing layer, a separating layer, one or two active ingredient-containing matrices having a pressure-sensitive adhesive surface, and a detachable protective sheet.

3. The transdermal therapeutic system according to claim 1, wherein the weight per unit area of the UV absorber-containing layer is from 5 to 50 g/m$^2$.

4. The transdermal therapeutic system according to claim 1, wherein the separating layer consists of a barrier polymer selected from the group consisting of polyethylene terephthalate, polyacrylonitrile, polyvinyl chloride, polyvinylidene chloride and their copolymers and colaminates.

5. The transdermal therapeutic according to claim 1, wherein an active ingredient-containing matrix and/or a UV absorber-containing layer is/are self-adhesive and comprise a polymer selected from the group consisting of polyisobutylene, polybutene and combinations thereof.

6. The transdermal therapeutic system according to claim 1, wherein the weight per unit area of the one or more active ingredient-containing matrices is from 30 to 150 g/m$^2$.

7. The transdermal therapeutic system according to claim 1, wherein the backing layer is permeable to an active ingredient in the one or more active ingredient-containing matrices, and the backing layer comprises polypropylene, polyethylene, polyurethane, ethylene/vinyl acetate copolymer or a multilayer composite of these materials with one another.

8. The transdermal therapeutic system according to claim 1, wherein a UV absorber is present in dissolved form in the one or more UV absorber-containing adhesive layers in a concentration of from 0.5 to 10% (m/m).

9. The transdermal therapeutic system according to claim 1, wherein exclusively the one or more UV absorber-containing layers contain a UV absorber.

10. The transdermal therapeutic system according to claim 1, wherein the one or more UV absorber-containing layers contain a UV absorber selected from the group consisting of p-aminobenzoic acid, 2-ethylhexyl 4-dimethylaminobenzoate, polyethoxyethyl 4-bis(polyethoxyl)aminobenzoate, cinnamic acid, isoamyl 4-methoxycinnamate, 2-ethylhexyl 4-methoxycinnamate, 3-benzylidenebornan-2-one, 3-(4')-methylbenzylindenebornan-2-one, 3-(4-sul-phone)benzylindenebornan-2-one, 3-(4'-trimethylammonium)benzylidenebornan-2-one methylsulphate, 4-isopropylbenzyl salicylate, 2-ethylhexyl salicylate, 3,3,5-trimethylcyclohexyl salicylate, 2-(5-chloro-2H-benzotriazole-2-yl)-6-(1,1-dimethylethyl)-4-methylphenol, 2,4,6'-trianiline-p-(carbo-2'-ethylhexyl-1'-oxy)-1,3,5-triazine, 3-imidazol-4-ylacrylic acid, 3-imidazol-4-yl-3-imidazol-4-ylacrylic ester, 2-phenylenebenzimidazole-5-sulphonic acid and its K, Na and triethanolamine salts, 2-cyano-3,3-diphenylacrylic acid, terephthaloylidenedicamphorsulphonic acid, butylmethoxydibenzoylmethane, benzophenone, benzophenone-3, benzophenone-4 and combinations thereof.

11. The transdermal therapeutic system according to claim 1, wherein the one or more UV absorber-containing layers is/are colourless or yellow.

12. The transdermal therapeutic system according to claim 1, wherein the system is transparent.

13. The transdermal therapeutic system according to claim 1, wherein the active ingredient comprises at least one hormone.

14. The transdermal therapeutic system according to claim 1, wherein the one or more active ingredient-containing matrices comprise gestodene, levonorgestrel or both.

15. The transdermal therapeutic system according to claim 1, wherein the transdermal therapeutic system has no membrane controlling the release of active ingredient.

16. The transdermal therapeutic system according to claim 1, consisting of the following sequence of layers: a backing layer, a UV absorber-containing layer, a separating layer, an active ingredient-containing matrix having a pressure-sensitive adhesive surface, and, optionally, a detachable protective sheet.

17. The transdermal therapeutic system according to claim 1, wherein the active ingredient comprises gestodene.

18. The transdermal therapeutic system according to claim 1, wherein said separating layer comprises a polyethylene terephthalate barrier polymer.

19. The transdermal therapeutic system according to claim 1, wherein said backing layer comprises a polyethylene.

20. The transdermal therapeutic system according to claim 17, wherein the active ingredient comprises gestodene.

21. The transdermal therapeutic system according to claim 20, wherein the system is transparent.

22. The transdermal therapeutic according to claim 21, wherein an active ingredient-containing matrix and/or a UV absorber-containing layer is/are self-adhesive and comprise a polymer selected from the group consisting of polyisobutylene, polybutene and combinations thereof.

* * * * *

UNITED STATES PATENT AND TRADEMARK OFFICE
CERTIFICATE OF CORRECTION

| | | |
|---|---|---|
| PATENT NO. | : 8,486,443 B2 | Page 1 of 1 |
| APPLICATION NO. | : 10/545826 | |
| DATED | : July 16, 2013 | |
| INVENTOR(S) | : Schumacher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2247 days.

Signed and Sealed this
Thirteenth Day of January, 2015

Michelle K. Lee
*Deputy Director of the United States Patent and Trademark Office*